United States Patent
Jacobsen et al.

[11] Patent Number: 6,007,310
[45] Date of Patent: Dec. 28, 1999

[54] VOLUMETRIC PUMP WITH STERILITY SEAL

[75] Inventors: Stephen C. Jacobsen; Clark C. Davis, both of Salt Lake City, Utah

[73] Assignee: Sarcos, LC, Salt Lake City, Utah

[21] Appl. No.: 08/862,972

[22] Filed: May 23, 1997

Related U.S. Application Data

[63] Continuation-in-part of application No. 08/157,693, Nov. 23, 1993, Pat. No. 5,632,606.

[51] Int. Cl.$^6$ .............................. F04B 17/00; F01B 9/00; F61H 21/22

[52] U.S. Cl. .......................... 417/362; 417/415; 92/137; 92/140; 92/168; 92/DIG. 4; 74/44; 74/89.15; 74/89.2

[58] Field of Search ..................... 417/415–417, 417/362; 277/152, 212 C; 92/168, 140, DIG. 4, 137; 74/44, 89.15, 89.2

[56] References Cited

U.S. PATENT DOCUMENTS

| | | |
|---|---|---|
| 247,360 | 9/1881 | Jay . |
| 695,589 | 3/1902 | Storle . |
| 789,430 | 5/1905 | Jewson . |
| 1,032,187 | 7/1912 | Clifford . |
| 1,032,344 | 7/1912 | Purpura ..................... 92/140 |
| 1,460,628 | 7/1923 | Wertz . |
| 1,536,415 | 5/1925 | Beck et al. . |
| 1,815,907 | 7/1931 | Halstead et al. . |
| 2,022,443 | 11/1935 | Stollberg . |
| 2,393,442 | 1/1946 | Yellott et al. . |
| 2,501,707 | 3/1950 | Bent et al. . |
| 2,613,027 | 10/1952 | Baumgart et al. ............ 92/140 |
| 2,645,449 | 7/1953 | Gulick . |
| 2,653,580 | 9/1953 | Moore, Jr. . |
| 2,709,118 | 5/1955 | Martin . |
| 2,750,746 | 6/1956 | Brannen . |
| 2,766,701 | 10/1956 | Giraudeau . |
| 2,782,801 | 2/1957 | Ludwig . |
| 2,856,961 | 10/1958 | Kruschik . |
| 3,014,463 | 12/1961 | Krohm ........................ 92/137 |
| 3,019,739 | 2/1962 | Prosser . |
| 3,095,785 | 7/1963 | Cahill . |
| 3,177,780 | 4/1965 | Andersen et al. . |
| 3,208,388 | 9/1965 | Glasgow ..................... 417/362 |
| 3,216,332 | 11/1965 | de Chambeau . |
| 3,268,201 | 8/1966 | Little . |
| 3,275,331 | 9/1966 | Mastrobattista et al. . |
| 3,300,703 | 1/1967 | Gold et al. . |
| 3,414,693 | 12/1968 | Watson et al. . |
| 3,463,193 | 8/1969 | Yost . |
| 3,509,890 | 5/1970 | Phillips . |
| 3,510,177 | 5/1970 | Shimula . |
| 3,515,169 | 6/1970 | Berg et al. . |
| 3,552,441 | 1/1971 | Luhleich . |
| 3,648,568 | 3/1972 | Wright . |
| 3,742,822 | 7/1973 | Talbert . |
| 3,802,805 | 4/1974 | Roeser . |
| 3,847,453 | 11/1974 | Herbert . |

(List continued on next page.)

*Primary Examiner*—Charles G. Freay
*Attorney, Agent, or Firm*—Thorpe, North & Western, LLP

[57] ABSTRACT

A volumetric pump for administering intravenous fluids to a patient includes a first housing having an elongate cavity therein with an open and a closed end. A resilient sheet of material having a centrally-located aperture covers the open end, and a pump shaft is slidably disposed through the aperture to form a sphincter seal therebetween. An inlet conduit leading from a fluid source (an IV bag) passes through the housing into the cavity near the open end thereof, and an outlet conduit leading to a fluid sink (the patient) passes through the housing from the cavity near the closed end thereof. A drive shaft is attached to the pump shaft to drive it back and forth in reciprocating motion inwardly and outwardly of the cavity to produce, respectively, a positive pressure forcing fluid out of the outlet conduit to the fluid sink, and a negative pressure forcing fluid from the fluid source through the inlet conduit. A second housing encloses the first housing and pump shaft, and includes a seal formed about the drive shaft to seal the inside of the second housing from the outside.

12 Claims, 2 Drawing Sheets

U.S. PATENT DOCUMENTS

| | | | |
|---|---|---|---|
| 3,918,683 | 11/1975 | Millar | 417/415 |
| 4,042,248 | 8/1977 | Williamitis . | |
| 4,055,107 | 10/1977 | Bartley . | |
| 4,085,941 | 4/1978 | Wilkinson et al. . | |
| 4,089,349 | 5/1978 | Schenk . | |
| 4,095,566 | 6/1978 | Fox . | |
| 4,128,227 | 12/1978 | Blomqvist . | |
| 4,159,024 | 6/1979 | Getman . | |
| 4,197,786 | 4/1980 | Pillon . | |
| 4,222,575 | 9/1980 | Sekiguchi et al. . | |
| 4,241,644 | 12/1980 | Schertler . | |
| 4,280,741 | 7/1981 | Stoll . | |
| 4,384,511 | 5/1983 | Mefferd . | |
| 4,392,034 | 7/1983 | Payne . | |
| 4,433,795 | 2/1984 | Maiefski et al. . | |
| 4,437,821 | 3/1984 | Ogawa . | |
| 4,448,425 | 5/1984 | von Bergen . | |
| 4,449,717 | 5/1984 | Kitawaki et al. . | |
| 4,468,170 | 8/1984 | Hanset . | |
| 4,549,718 | 10/1985 | Seger . | |
| 4,627,795 | 12/1986 | Schmitz-Montz . | |
| 4,637,295 | 1/1987 | Powers et al. . | |
| 4,674,965 | 6/1987 | Hasegawa et al. . | |
| 4,721,133 | 1/1988 | Sundblom . | |
| 4,723,755 | 2/1988 | Ishigaki . | |
| 4,751,867 | 6/1988 | Johansson et al. . | |
| 4,759,553 | 7/1988 | Goodman et al. . | |
| 4,804,913 | 2/1989 | Shimizu . | |
| 4,900,883 | 2/1990 | Brame et al. . | |
| 4,974,755 | 12/1990 | Sonntag . | |
| 4,975,679 | 12/1990 | Ballyns . | |
| 5,104,374 | 4/1992 | Bishko et al. . | |
| 5,140,113 | 8/1992 | Machado . | |
| 5,144,882 | 9/1992 | Weissgerber . | |
| 5,199,718 | 4/1993 | Nieniec . | |
| 5,267,721 | 12/1993 | Stroh . | |
| 5,380,017 | 1/1995 | Leeuwenburg et al. . | |
| 5,429,602 | 7/1995 | Hauser . | |
| 5,440,968 | 8/1995 | Sekine . | |
| 5,467,689 | 11/1995 | Carlin et al. . | |
| 5,632,606 | 5/1997 | Jacobsen et al. | 417/415 |
| 5,769,615 | 6/1998 | Giter | 417/415 | ic pump, suitable for a variety of uses including medical

VOLUMETRIC PUMP WITH STERILITY SEAL

This is a continuation-in-part of application Ser. No. 08/157,693, filed Nov. 23, 1993, now U.S. Pat. No. 5,632,606.

BACKGROUND OF THE INVENTION

This invention relates to a lightweight, inexpensive volumetric pump, suitable for a variety of uses including medical systems such as intravenous (IV) therapy systems and the like, and including an enclosure about the pump to maintain it free of contamination.

The intravenous administration of fluids to patients is a well-known medical procedure for, among other things, administering life sustaining nutrients to patients whose digestive tracts are unable to function normally due to illness or injury, administering antibiotics to treat a variety of serious infections, administering analgesic drugs to patients suffering from acute or chronic pain, administering chemotherapy drugs to treat patients suffering from cancer, etc.

The intravenous administration of drugs frequently requires the use of an IV pump connected or built into a so-called IV administration set including, for example, a bottle of fluid to be administered and typically positioned upside down, a sterile plastic tubing set, and a pump for pumping fluid from the bottle through the IV set to the patient. Other mechanisms may be included to manually stop the flow of fluid to the IV feeding tube and possibly some monitoring devices.

Current IV pumps generally are of two basic types: electronic pumps and disposable non-electronic pumps. Although the electronic pumps have been significantly miniaturized and do include some disposable components, they are nevertheless generally high in cost, require frequent maintenance with continued use, and may be difficult for a layman to operate if, for example, self treatment is desired.

A problem common to both type pumps is the susceptibility to external contamination or interference, a problem which is especially acute in medical applications such as an IV pump.

SUMMARY OF THE INVENTION

It is an object of the invention to provide a new and improved volumetric pump which is especially suitable for use in IV administration sets, other medical systems, and the like.

It is a further object of the invention to provide such a pump which may be readily maintained free of contamination.

The above and other objects of the invention are realized in a specific illustrative embodiment of a pump having a housing defining an elongate cavity therein, with an opening on one side of the housing adjacent to and in communication with the one end, the other end being closed. Also included is a resilient sheet of material disposed over the opening in the housing, with the sheet including an aperture positioned in alignment with the cavity at the one end thereof. An elongate shaft is slidably disposed in the aperture so that one end of the shaft extends into the cavity and the other end extends out of the housing. An inlet is provided in the housing, through which fluid from a fluid source may flow into the cavity, and an outlet is also provided in the housing, through which fluid may flow from the cavity to a fluid sink. The resilient sheet of material surrounds and grips the shaft at the aperture in the sheet to provide a sphincter seal which prevents fluid from flowing through the aperture but allows the shaft to slide longitudinally therein.

When the shaft is moved in a direction outwardly of the housing, a negative pressure is produced in the cavity to draw in fluid through the inlet, and when the shaft is moved further into the cavity, a positive pressure is produced in the cavity to force fluid from the cavity through the outlet. Valves may be provided in or near the inlet and outlet to allow fluid only to flow into the cavity through the inlet and out of the cavity through the outlet.

A variety of driver mechanisms and control methods may be provided to cause the shaft to reciprocate within the cavity to produce the pumping action, including ratchet drives, magnetic linear step motors, rotary-to-linear crank drives, and screw drive mechanisms, all of which would likely require a drive rod, drive current supply cables or other drive access means extending to near or at that end of the shaft which is outside of the housing. An enclosure surrounds the housing, shaft and a portion of the drive access means, to seal the enclosed items from outside contamination or interference.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION OF THE DRAWINGS

Figure 1:
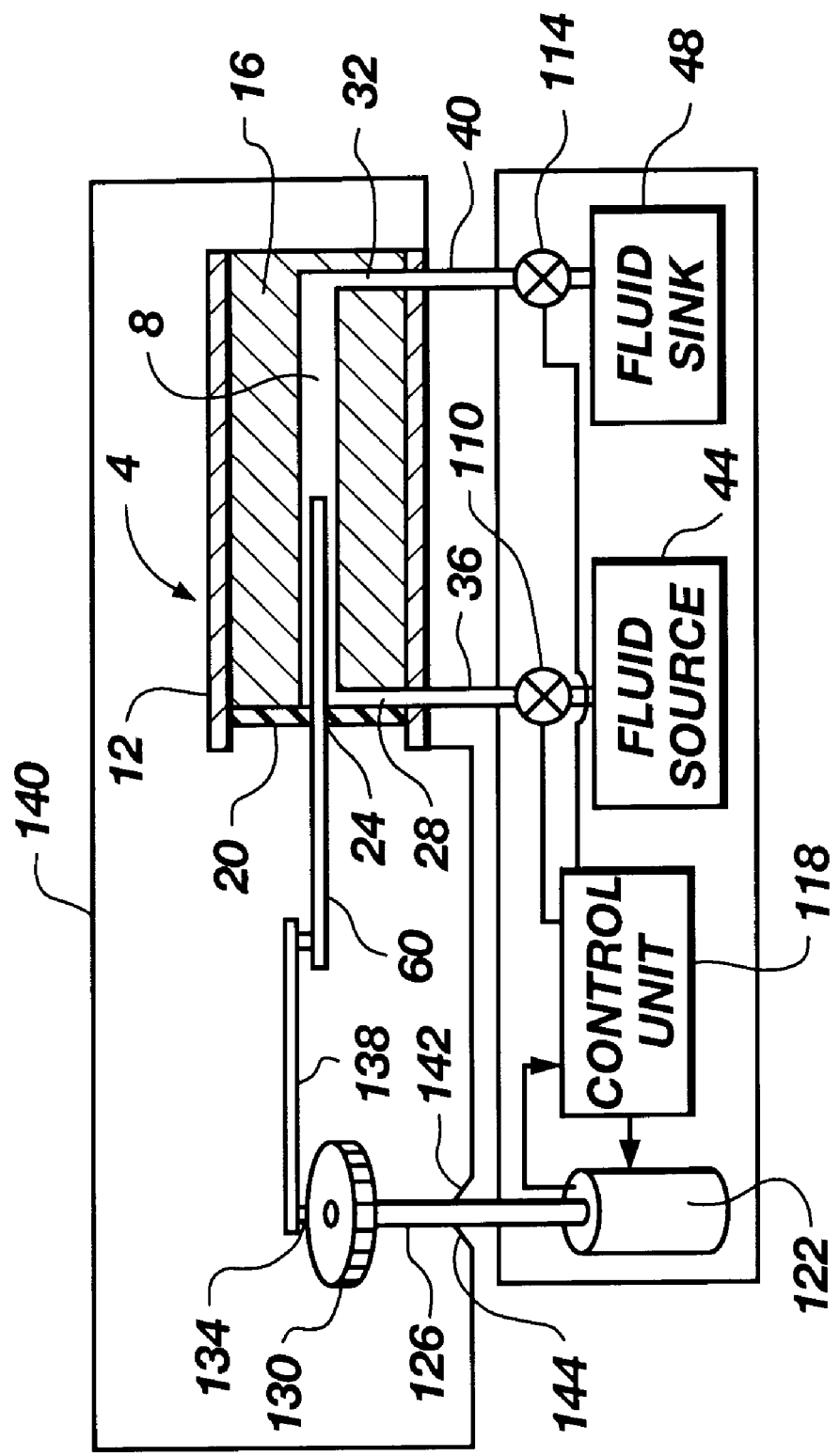
FIG. 1 is a side, cross-sectional, schematic view of an embodiment of a volumetric pump with sterility seal made in accordance with the principles of the present invention.

Referring to FIG. 1, there is shown a side, cross-sectional, schematic view of an embodiment of a volumetric pump in which includes a housing structure 4, formed with an elongate cavity 8. The housing 4 might illustratively be formed with an exterior shell 12 made of metal or hard plastic, and an interior filler 16 disposed against the shell 12, with the cavity 8 formed centrally therein. The filler could similarly be metal or hard plastic.

Disposed in one end of the housing 4 is a resilient sheet of material 20, made, for example, of latex rubber, silicon rubber, or nitrile rubber. The sheet of material 20 fills the end of the housing 4 to prevent communication between the outside of the housing and the cavity 8 except through an aperture 24 positioned in line with the cavity 8.

An inlet duct 28 is formed in the housing 4 generally adjacent to the sheet of material 20, to communicate with the cavity 8, and an outlet duct 32 is similarly formed in the housing to communicate with the cavity at the other end thereof. Conduits 36 and 40 respectively couple ducts 28 and 32 to a fluid source 44 and a fluid sink 48. Valves 110 and 114 are disposed respectively in the conduits 36 and 40 to allow fluid to flow from the fluid source 44 into the cavity 8, and to allow fluids to flow from the cavity 8 to the fluid sink 48, under control of a control unit 118.

The control unit 118 also controls operation of an electric motor 122 whose drive shaft 126 is coupled to a drive wheel 130. As the motor 22 operates to rotate the drive shaft 126, the wheel 130 is rotated. A drive nipple 134 is mounted near the perimeter of the drive wheel 130 and is pivotally coupled to one end of a drive shaft 138 which, in turn, is pivotally coupled at its other end to the free end of the pump shaft 60. As the drive wheel 130 is caused to rotate, the drive shaft 138 is caused to reciprocate back and forth and, in turn, cause the shaft 60 to reciprocate in the cavity 8.

A second housing 140 is provided in the preferred embodiment around the housing 4, pump shaft 60, drive shaft 138, drive wheel 130, and a portion of the drive shaft 126, to seal the components from outside contamination or interference. The housing 140 preferably comprises rigid material such as steel or plastic except around the drive shaft 126, where it comprises a sheet of resilient material 142, similar to the sheet 20, with an aperture 144 formed therein to create a sphincter seal on the drive shaft 126 similar to the seal of the sheet 20 around the pump shaft 60. However, in the cast of the drive shaft 126, the sheet 142 at the aperture 144 seals the drive shaft 126 during rotational, rather than reciprocal, movement.

In operation, the control unit 118 causes the motor 122 to operate and rotate, with the angular position of the drive shaft 126 being fed back to the control unit. Based on the angular position of the drive shaft 126 and thus the drive wheel 130, the control unit will cause valves 110 and 114 to alternately open and close to allow fluid to flow from the fluid source 44 into the cavity 8 on the withdrawal stroke or movement of the shaft 60 (to the left in FIG. 1), and allow fluid to flow from the cavity 8 to the fluid sink 48 on the pump stroke of the shaft 60 (to the right in FIG. 1). In effect, more direct control of the opening and closing of the valves 110 and 114 is provided to ensure more effective pumping of fluid from the fluid source 44 to the fluid sink 48 by preventing free flow caused when both valves are open at the same time (which might occur, for example, if the fluid source were an IV bag and the IV bag was squeezed). The control unit 118 might illustratively be any conventional microprocessor used for controlling operation of electrical equipment.

FIGS. 2, 3, 4, 5 and 6 show five illustrative embodiments of drive mechanisms which may be used to drive the pump or valve shafts of the present invention.

Figure 2:
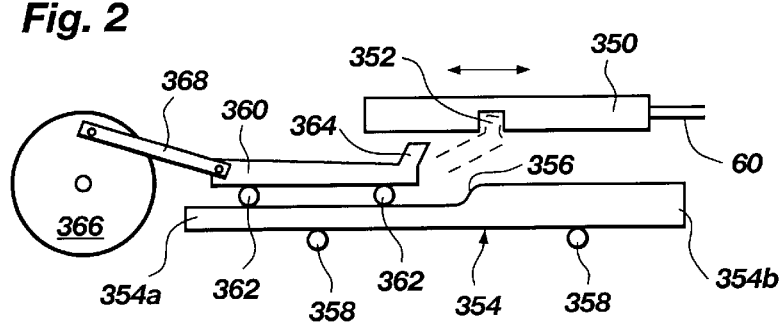
FIGS. 2, 3, 4, 5 and 6 show five illustrative embodiments of drive mechanisms which may be utilized for driving the pump shaft of the volumetric pump of the present invention.

FIG. 2 shows a side view of a drive mechanism which includes an elongate drive shaft 350 attached to a pump or valve shaft 60, with a notch 352 cut on the bottom of the drive shaft 350. A ramp 354 containing a shoulder 356 is disposed beneath the drive shaft 350. The shoulder 356 divides the ramp into a lower portion 354*a* and a higher portion 354*b*. Rollers 358 or other suitable adjustment means are disposed on the underside of the ramp to allow adjusting its longitudinal position to thus vary the stroke length of the pump shaft 60, as described below. A secondary driver 360 is disposed on rollers 362 which rest on the lower portion 354*a* of the ramp. A tab 364 extends upwardly from the forward end of the secondary driver nearest the shoulder 356. A disc 366 given rotary motion by a motor or other drive means connects to the end of the secondary driver opposite the tab 364 by a rod 368, which is pivotally attached at one end to the disc and at the other to the secondary driver. The rotary motion of the disc 366 moves the secondary driver 360 back and forth in a conventional manner.

In operation, when the secondary driver 360 moves forward, it does not contact the drive shaft 350 until the rollers 362 reach and move up the shoulder 356, forcing the secondary driver 360 upwardly and the tab 364 into the notch 352, causing the drive shaft 350 to be moved forwardly with the secondary driver 360. When the secondary driver 360 moves rearward, it forces the drive shaft 350 rearward by way of the tab/notch connection until the rollers 362 move down the shoulder 356, causing the tab 364 to come out of the notch 352, breaking the connection and stopping movement of the drive shaft 350.

As will be apparent to those skilled in the art, the notch 352 must initially be placed in position to receive the tab 364 when the latter is elevated by the shoulder 356.

The stroke of the drive shaft 350 may be easily adjusted by moving the ramp 354 forwardly or rearwardly. If the ramp is moved rearwardly (with appropriate adjustment of the drive shaft 350 to align the notch), the tab 364 enters the notch earlier in the forward movement of the secondary driver 360, moving the drive shaft farther forward, and correspondingly farther rearward. If the ramp is moved forwardly, the tab enters the notch later in the forward movement of the secondary driver 360, moving the drive shaft a lesser distance forward and a correspondingly lesser distance rearward.

Varying the stroke of the drive shaft 350 adjusts the flow rate of the pump while allowing the driver to be run at a constant rate. Other control or drive mechanisms may be used to accomplish the same end (i.e., adjust the flow rate) such as variable speed drive mechanisms, and variable delay of constant speed drive mechanisms.

Figure 3:
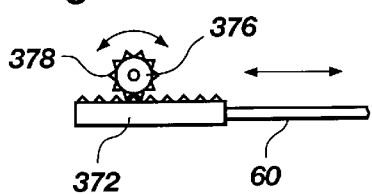

FIG. 3 shows another drive mechanism comprising a pump or valve shaft 60 driven by a drive shaft 372 having teeth 374 on one side. A wheel 376 having teeth 378 spaced circumferentially therearound engages the teeth 374, converting rotary movement of the wheel into longitudinal movement of the drive shaft. The rotary movement of the wheel reverses direction to reverse direction of the drive shaft.

Figure 4:
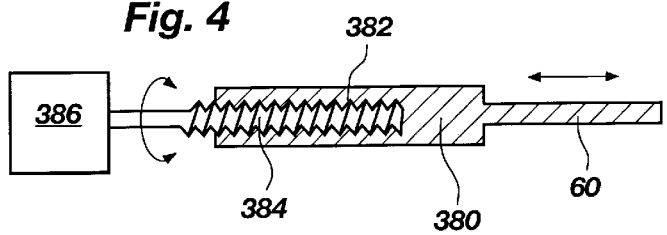

FIG. 4 shows another drive mechanism comprising an elongate drive shaft 380 connected to a pump or valve shaft 60. The drive shaft 380 has a threaded interior recess 382 into which a threaded rod 384 fits. The rod is caused to rotate by a motor 386. Depending on the direction of rotation, the rotational motion of the rod 384 moves the drive shaft 380 back or forth.

Figure 5:
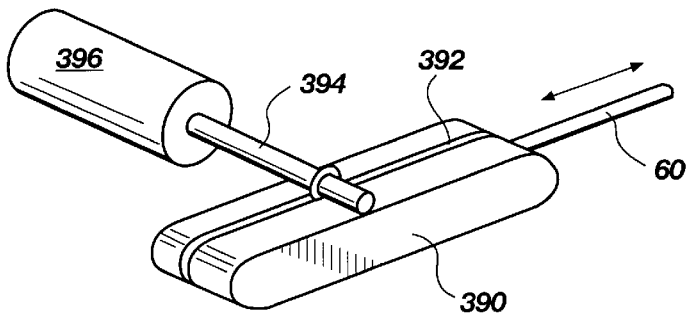

FIG. 5 shows a perspective view of another drive mechanism for a pump shaft 60 attached at one end to a rigid anvil 390 which is oval-shaped in side cross section. A flexible filament 392 made of suitably strong material is wrapped snugly around the anvil, with a loop of the filament wrapped around a drive shaft 394 which is given rotational motion by a motor 396. As the drive shaft rotates to thus move the filament 392, the anvil and thus the pump shaft are caused to move longitudinally, as the drive shaft 394 gathers in and lets out filament 392 to accommodate its rotational movement, the manipulated filament forces the anvil to move in turn.

Figure 6:
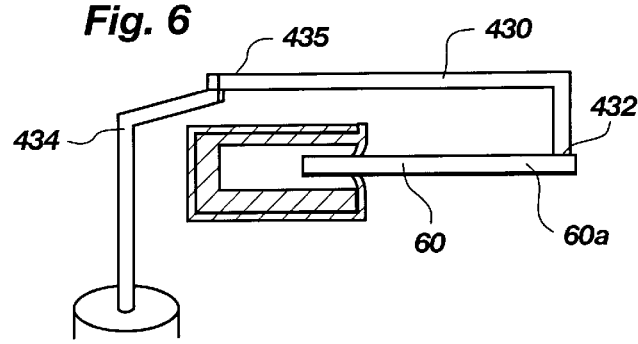

FIG. 6 shows a plunger 60 driven by a drive shaft 430 which is pivotally connected at an outer end 60*a* to an end 432 of the drive shaft. A crank 434 is pivotally connected to the other end 435 of the drive shaft 430. The crank is rotated by any suitable means, moving the drive shaft 430 in a reciprocating fashion and thus the plunger 60 back and forth in longitudinal movement. Preferably, sphincter seals as described above are formed at fluid interfaces with the components.

For all of the above-described drive mechanisms, the primary components of the pump would be enclosed by a housing similar to housing 140 of FIG. 1, which, in turn, would include a seal similar to the seal formed by the resilient material 142 with aperture 144 of FIG. 1 formed around a drive element of the drive mechanism. For example, the sterility housing seal could be formed around a shaft 366a of the mechanism of FIG. 2 which shaft drives the disk 366. In the FIG. 3 mechanism, the seal could be formed around a drive shaft 379 which drives the wheel 376. For the FIG. 4 apparatus, the sterility seal could be formed around the non-threaded portion 384a of the threaded rod 384. In the FIG. 5 apparatus, the sterility seal would be formed around drive shaft 394 and in FIG. 6, the sterility seal would be formed around the shaft 434a of the crank 434.

The embodiments of the invention described herein are only examples of how the invention may be applied to specific devices. Modifications and variations of, for example, materials used, sizes and shapes of components, and equivalent structures will be apparent to those skilled in the art while remaining within the scope of the invention.

We claim:

1. A volumetric pump comprising a pump mechanism operable to pump fluid from a fluid source to a fluid sink, said pump mechanism comprising a housing and a pump shaft, actuation means coupled to said pump shaft and configured to cause the pump shaft to move to operate the pump mechanism, a moveable shaft coupled at a first end to said actuation means, and enclosure means enclosing the pump mechanism, actuation means, and part of the moveable shaft, and including a sphincter seal for sealing about the moveable shaft which extends therethrough, from outside the enclosure means to the inside thereof, thereby sealing the pump mechanism from outside contamination.

2. A volumetric pump as in claim 1 wherein the sphincter seal comprises a resilient sheet of material formed as part of the enclosure means, and including an aperture through which the moveable shaft extends.

3. A volumetric pump as in claim 2 wherein the dimension of the cross-section of the aperture is smaller than the dimension of the cross-section of the moveable shaft.

4. A volumetric pump as in claim 1 wherein the enclosure means is generally rigid.

5. The pump of claim 1 wherein the actuation means comprises elongate drive means attached to the end of the pump shaft outside the housing, and a rotatable wheel attached to the moveable shaft which, when rotated, engages the drive means along the length thereof to cause the drive means and thus the pump shaft to move longitudinally.

6. The pump of claim 1 wherein the actuation means comprises an elongate drive shaft attached at one end to the end of the pump shaft outside the housing, said drive shaft including a threaded recess formed in the other end thereof, and wherein said moveable shaft comprises a rotatable rod inserted in the recess and including threads complimentary with the threads in the recess, whereby the rotation of the rod causes longitudinal movement of the drive shaft.

7. The pump of claim 1 wherein the actuation means comprises an anvil connected to the end of the pump shaft outside the housing, a filament snugly disposed around the anvil and substantially parallel to the pump shaft, and wherein said moveable shaft comprises a rotatable rod, substantially perpendicular to the anvil, inserted in a loop in the filament such that rotation of the rod causes longitudinal, reciprocal movement of the anvil, and thus of the pump shaft.

8. The pump of claim 1 wherein the actuation means comprises elongate drive means pivotally connected at a first end to the end of the pump shaft outside the housing, a substantially L-shaped rotatable crank pivotally connected at one end to a second end of the drive means and at the other end to said moveable shaft, so that when the moveable shaft and thus the crank are rotated, the drive means and thus the pump shaft are caused to move longitudinally in a reciprocal fashion.

9. A pump for pumping fluids from a fluid source to a fluid sink comprising a first housing defining an elongate cavity therein, with an opening on one side of the housing adjacent to and in communication with one end of the cavity, the other end being closed, a resilient sheet of material disposed over the opening in the housing, said sheet including an aperture positioned in alignment with the cavity at said one end thereof, an elongate shaft slidably disposed in the aperture so that one end of the shaft extends into the cavity and the other end extends out of the housing, said aperture having substantially the same cross-sectional shape as that of the shaft, and the same cross-sectional dimensions or smaller, inlet means for conveying fluid from the fluid source into the cavity when a negative pressure is produced therein, outlet means for carrying fluid from the cavity to the fluid sink when a positive pressure is produced in the cavity, actuation means for causing the shaft to reciprocate longitudinally in the cavity, sliding back and forth in the aperture, to alternately produce a negative pressure and positive pressure in the cavity, and a second housing enclosing the first housing and the elongate shaft, surrounding the inlet means and outlet means, and including a seal formed about the actuation means to prevent passage of air from outside the second housing to the inside.

10. The pump of claim 9 wherein said seal comprises a second resilient sheet of material having an opening in which the actuation means is disposed.

11. A pump as in claim 10 wherein said second resilient sheet of material is a material selected from the group consisting of latex rubber, silicone rubber and nitrile rubber.

12. A pump as in claim 10 wherein the dimensions of the cross-section of the opening in the second resilient sheet of material are smaller than the dimensions of the cross-section of the actuation means about which the second resilient sheet of material is disposed.

* * * * *